United States Patent
Warrington et al.

(10) Patent No.: US 6,841,348 B1
(45) Date of Patent: Jan. 11, 2005

(54) METHODS FOR IDENTIFYING AND USING MAINTENANCE GENES

(75) Inventors: Janet A. Warrington, Los Altos, CA (US); Mamatha Mahadevappa, Cupertino, CA (US); Archana Nair, The Woodlands, TX (US)

(73) Assignee: Affymetrix, Inc., Santa Clara, CA (US)

( * ) Notice: Subject to any disclaimer, the term of this patent is extended or adjusted under 35 U.S.C. 154(b) by 209 days.

(21) Appl. No.: 09/693,204

(22) Filed: Oct. 19, 2000

Related U.S. Application Data

(60) Provisional application No. 60/161,000, filed on Oct. 21, 1999.

(51) Int. Cl.$^7$ .............................. C12Q 1/68; C12P 19/34; C07H 21/04
(52) U.S. Cl. ........................ 435/6; 435/91.5; 435/91.51; 536/23.1; 536/23.2; 536/23.5
(58) Field of Search ........................ 435/6, 91.5, 91.51; 536/23.1, 23.2, 23.5

(56) References Cited

U.S. PATENT DOCUMENTS

| | | | |
|---|---|---|---|
| 6,221,600 B1 * | 4/2001 | MacLeod et al. ............... | 435/6 |
| 6,245,517 B1 * | 6/2001 | Chen et al. ..................... | 435/6 |

OTHER PUBLICATIONS

Kagawa, Y., et al., Regulation of Mitochondrial ATP Synthesis in Mammalian cells . . . vol. 22, No. 3 pp 219–229 (1990).*

Adjaye et al., "cDNA Libraries from Single Human Preimplantation Embryos", *Genomics 46*, 1997, pps. 337–344.

Adjaye et al., "The Construction of cDNA Libraries from Human Single Preimplantation Embryos and Their Use in the Study of Gene Expression During Development", *Jrnl. Of Assisted Reproduction and Genetics*, vol. 15, No. 5, 1998, pps. 344–348.

de Boer et al., "The NADH–specific enoyl–acyl carrier protein reductase: Characterization of a housekeeping gene involved in storage lipid synthesis in seeds of arabidopsis and other plant species", *Plant Physiol. Biochem*, vol. 36, No. 7, 1998, pps. 473–486.

Koning et al., "Analysis of cytokine gene expression in stimulated T cells of small children by semiconductor–quantitative PCR", *Mediators of Inflammation*, vol. 4, 1995, pps. 196–204.

Warrington et al., "Identification and comparison of housekeeping/maintenance genes in normal adult and fetal tissue", *The Amer. Jrnl of Human Genetics*, Slide Session 34: Genomics I, vol. 65, No. 4, Oct. 1999, pp. A28.

* cited by examiner

*Primary Examiner*—Diana B. Johannsen
(74) *Attorney, Agent, or Firm*—Sandra E. Wells; Philip L. McGarrigle

(57) ABSTRACT

This invention provides methods for discovering maintenance genes and for using maintenance genes. In one embodiment, the expression of at least three maintenance genes are measured and used as reference (or control) for comparing the expression of target genes in two or more biological samples.

2 Claims, No Drawings

METHODS FOR IDENTIFYING AND USING MAINTENANCE GENES

RELATED APPLICATIONS

This application claims the priority of U.S. Provisional Application No. 60/161,000, filed on Oct. 21, 1999. The 60/161,000 application is incorporated herein by reference in its entirety.

This application is related to U.S. Pat. No. 6,033,860 which is incorporated herein by reference in its entirety.

BACKGROUND OF THE INVENTION

This application provides methods, compositions for identifying and using maintenance genes. The methods and compositions have extensive practical applications in areas such as drug discovery and diagnostics.

Housekeeping genes, or maintenance genes, are those genes constitutively expressed to maintain cellular function (See, Watson, J. D., N. H. Hopkins, J. W. Roberts, J. A. Steitz, A. M. Weiner, A. M. *Molecular Biology of the Gene*, Vol. 1, 1965).

Previously tons of genes have been reported as putative housekeeping genes. The genes previously reported were identified by conventional methods and the putative housekeeping role of the gene product is an incidental observation (Duhig, T., C.

Ruhrberg, O. Mor, M. Fried. The Human Surfeit Locus. *Genomics,* 52(1) 72–78, 1998; Hampsey, M. Molecular Genetics of the RNA Polymerase II General Transcriptional Machinery. *Microbiol. Mol. Biol. Rev.* 62(2):465–503, 1998; May, B. K., C. R. Bhasker, T. C. Cox. Molecular Regulation of 5-Amniolevulinate Synthase Diseases Related to Heme Biosynthesis. *Mol. Biol. Med.,* 7(5):405–421, 1990; Milner, C. M., R. D. Campbell.

Genes, Genes and More Genes in the Human Major Histocompatibility Complex. *Bioessays,* 14(8):565–571, 1992; Rifkind, R. A., P. A. Marks, A. Bank, M. Terada, G. M.

Maniatis, F. E. Reuben, E. Fibach. Erythroid Differentiation and the Cell Cycle: Some Implications from Murine Foetal and Erythroleukemic Cells. *Ann.Immunol.*127:887–893, 1976; Roberston, H. A. Immediate-Early Genes, Neuronal Plasticity, and Memory.

Biochem. *Cell Biol.,* 70(9): 729–737, 1992; Russo-Marie, F. Macrophages and the Glucocorticoids. *J Neuroimmunol,* 40(2-3):281–286, 1992; Strehler, B. L., M. R. Freeman.

Randomness, Redundancy and Repair: Roles and Relevance to Biological Aging. *Mech.*

Aging Dev. 14(1-2) 15–38, 1980; and Yamamoto, T., Y. Matsui, S. Natori, M. Obinata.

Cloning of a Housekeeping-Type Gene (MER5) Preferentially Expressed in Murine Erythroleukemia Cells.*Gene* 80 2:337–343, 1989).

Recently, massive parallel gene expression monitoring methods have been developed to monitor the expression of a large number of genes using nucleic acid array technology which was described in detail in, for example, U.S. Pat. Nos. 5,871,928, 5,800,992 and 6,040,138; de Saizieu, et al., 1998, *Bacteria Transcript Imaging by Hybridization of total RNA to Oligonucleotide Arrays,* NATURE BIOTECHNOLOGY, 16:45–48; Wodicka et al., 1997*, Genome-wide Expression Monitoring in Saccharomyces cerevisiae,* NATURE BIOTECHNOLOGY 15:1359–1367; Lockhart et al., 1996, *Expression Monitoring by Hybridization to High Density Oligonucleotide Arrays.* NATURE BIOTECHNOLOGY 14:1675–1680; Lander, 1999*, Array of Hope,* NATURE-GENETICS, 21(suppl.), at 3.

SUMMARY OF THE INVENTION

In one aspect of the current invention, methods for identifying a gene are provided. The methods include the steps of determining the expression of at least one hundred genes in at least two different types of tissues in two different developmental stages; and indicating a gene that is expressed at the same level in the tissues in the stages as the maintenance gene. In some embodiments, the method involves determining the expression of one thousand genes. In some preferred embodiments, the expression of candidate maintenance genes are measured in at least five different types of tissues. In one preferred embodiment, gene expression is determined using nucleic acid probe arrays such as high density oligonucleotide probe arrays, optical fiber arrays, spotted arrays (oligonucleotide, cDNA clones, cDNA fragments, etc.).

In preferred embodiments, a gene is considered as expressed at the same level if the variation of its expression is within 2, 5 or 10 fold. In another preferred embodiment, a gene is considered as expressed at the same level if the variation of its expression is not statistically significant.

In another aspect of the invention, methods are provided for comparing the expression of a gene in a plurality of biological samples. The methods include measuring the expression of at least three, five, seven or ten maintenance genes selected from the group of genes listed in table 1 or subset of the genes from table 1. The methods further include a step of evaluating the expression of the gene in the plurality of samples using the expression of the at least three, five or ten, maintenance genes. In some embodiments, the expression of a gene is adjusted using the expression of maintenance genes as a control. For example, the expression measurement of a target gene may be divided by the expression measurements of maintenance genes.

DESCRIPTION OF THE INVENTION

Reference will now be made in detail to the preferred embodiments of the invention. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention.

Methods for Gene Expression Monitoring:

Various techniques for large scale polymer synthesis and probe array manufacturing are known. Some examples include the U.S. Pat. Nos. 5,143,854, 5,242,979, 5,252,743, 5,324,663, 5,384,261, 5,405,783, 5,412,087, 5,424,186, 5,445,934, 5,451,683, 5,482,867, 5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,753,788, 5,770,456, 5,831,070, and 5,856,011, all of which are incorporated by reference in their entirety for all purposes.

The hybridization conditions between probe and target should be selected such that the specific recognition interaction, i.e., hybridization, of the two molecules, is both sufficiently specific and sufficiently stable. See, e.g., Hames and Higgins (1985) Nucleic Acid Hybridisation: A Practical Approach, IRL Press, Oxford. These conditions will be dependent both on the specific sequence and often on the guanine and cytosine (GC) content of the complementary hybrid strands. The conditions may often be selected to be universally equally stable independent of the specific sequences involved. This typically will make use of a reagent such as an alkylammonium buffer. See, Wood et al. (1985) "Base Composition-independent Hybridization in Tetramethylammonium Chloride: A Method for Oligonucleotide Screening of Highly Complex Gene Libraries," Proc. Natl.

Acad. Sci. USA, 82:1585–1588; and Krupov et al. (1989) "An Oligonucleotide Hybridization Approach to DNA Sequencing," FEBS Letters, 256:118–122; each of which is hereby incorporated herein by reference. An alkylammonium buffer tends to minimize differences in hybridization rate and stability due to GC content. By virtue of the fact that sequences then hybridize with approximately equal affinity and stability, there is relatively little bias in strength or kinetics of binding for particular sequences.

Temperature and salt conditions along with other buffer parameters should be selected such that the kinetics of renaturation should be essentially independent of the specific target subsequence or oligonucleotide probe involved. In order to ensure this, the hybridization reactions will usually be performed in a single incubation of all the substrate matrices together exposed to the identical same target probe solution under the same conditions. The hybridization conditions will usually be selected to be sufficiently specific such that the fidelity of base matching will be properly discriminated. Of course, control hybridizations should be included to determine the stringency and kinetics of hybridization. See for example, U.S. Pat. No. 5,871,928 which is hereby incorporated in its entirety for all purposes. Another factor that can be adjusted to increase the ability of targets to hybridize to probes, is the use of nucleic acid analogs or PNAs in the probes.

They can be built into the probes to create a more uniform set of hybridization conditions across the entire array. See U.S. patent application Ser. No. 08/630,427 which is hereby incorporated by reference in its entirety for all purposes.

Samples are then washed and stained using a robotic liquid handling machine such as the GeneChip® Fluidic Station 400 (Affymetrix, Inc., Santa Clara, Calif.). Fluidics stations have been described in, for example, U.S. patent application No. 08/624,133 now abandoned and Ser. No. 09/070,689 now U.S. Pat. No. 6,114,122. Finally, samples are placed on an automated loader which interfaces with a scanner such as the GeneArray™ scanner (Agilent Technologies). Scanners have been described in, for example, U.S. Pat. Nos. 5,578,832, 5,834,7484 and 5,837,832, U.S. patent application Ser. Nos. 08/456,598, 09/238,131 now U.S. Pat. No. 6,225,625 now U.S. Pat. No. 6,270,644, Ser. No. 08/856,642 now U.S. Pat. No. 5,981,956, Ser. No. 09/295,214 now U.S. Pat. No. 6,207,960, Ser. No. 08/456,782 now abandoned, Ser. No. 08/999,188 now U.S. Pat. No. 6,491,811, U.S. Provisional Patent Application No. 60/106,397 and European Patent No. 97925605 each of which is hereby incorporated by reference in its entirety for all purposes.

The results are then analyzed using a computer program. Computer programs for the analysis of hybridization patterns on arrays have been described in, for example, U.S. Pat. Nos. 5,733,729, and 5,795,716, U.S. patent application Ser. No. 09/309,328 now U.S. Pat. No. 6,197,516, Ser. No. 09/020,743 now U.S. Pat. No. 6,420,108, Ser. No. 08/531,137 now U.S. Pat. No. 5,974,164, Ser. Nos. 09/158,765, 08/584,754, 09/049,805, 08/828,952, 08/948,896 and U.S. Provisional Patent Application Nos. 60/033,053 and 60/085,118 each of which is incorporated by reference in its entirety for all purposes.

Methods for Detecting Maintenance Genes:

The term housekeeping gene was broadly defined as a gene that is constitutively expressed. In this application, housekeeping genes are also referred to as maintenance genes. Generally, the housekeeping genes are critical to the processes that must be carried out for successful completion of the cell cycle and consequently play a key role in the activity and maintenance of every cell. It is likely that many genes may be constitutively expressed but in varying amounts in different tissues. These differences in level of abundance are probably more relevant to the characteristic function of each tissue than to the housekeeping/maintenance role.

Until recently the technical challenge of accurately measuring small differences in gene expression have been practically insurmountable, consequently there is little evidence to support the importance of small differences. One aspect of the invention provides methods, compositions, devices and algorithms for detecting Maintenance genes. The method comprises the step of measuring the expression of at least 50 genes, preferably 100 genes, more preferably more than 1000 genes, in a variety of tissues. The method further comprises the step of indicating that the gene is a Maintenance gene if the expression is the same in all the tissues of interest or in a subset of the tissues of interest.

The term tissue, as used herein, is intended to describe a biological material from an organism. Therefore, an organ (or a homogenate of the organ), such the liver or kidney, may be referred to as a tissue. The methods are most suitable for simultaneously detecting a large number Maintenance genes. When it is used for simultaneous determination of a large number of Maintenance genes, the method includes the step of simultaneous monitoring of the expression of a large number of genes. Methods for monitoring a large number of genes are well known in the art and are described, for example, in the background section, supra. In some embodiments, the expression of a gene in a number of tissue is measured. The gene is considered as expressed at the same level if it is expressed in all the tissues at levels within ten folds, preferably within fourfold and more preferably within two fold. In some embodiments, a gene is considered as expressed at the same level if it is expressed in all tissues with no statistically difference. In the example that follows, genes were considered as expressed at the same level if they were expressed in all seven tissues at levels within fourfold. For most genes differences less than fourfold are probably not biologically significant but there is not enough data to conclude that a five or six-fold difference is more biologically significant than a three or four-fold difference (Cho, R. J., M. J. Campbell, E. A. Winzeler, L. Steinmetz, A. Conway, L. Wodicka, T. G. Wolfsberg, A. E. Gabrielian, D. Landsman, D. J. Lockhart, R. W. Davis. A Genome-Wide Transcriptional Analysis of the Miotic Cell Cycle. *Molecular Cell,* 2:65–73, 1998; Creanor, J., J. M. Mitchinson. Nucleoside Diphosphokinase, An Enzyme With Step Changes in Activity During the Cell Cycle of the Fission Yeast *Schizosaccharomyces Pombe. Journal of Cell Science* 207–215, 1986; Klevecz, R. R. *The Scientist* 22–24, 1999; Klevecz, R. R., S. A. Kaufman, R. M. Shymko, Cellular Clocks and Oscillators. International Review of Cytology, 86:97–128, 1984). For a subset of genes it is likely that small differences have biological relevance such as the genes encoding proteins that function differently when bound to high affinity versus low affinity receptors or gene products triggering cellular cascades (Merchav, S. The Haematopoietic Effects of Growth Hormone and Insulin-Like Growth Factor-I. *J. Pediatr. Endocrin. Metab.* 11(6):677–685, 1998; Skerry, T. M. Identification of Novel Signaling Pathways During Functional Adaptation of the Skeleton to Mechanical Loading: The Role of Glutamate as a Paracrine Signaling Agent in the Skeleton. *J. Bone Miner Metab.* 17(1): 66–70, 1999).

Maintenance Genes:

In another aspect of the invention, a subset of genes expressed at the same level in each of seven major tissues are identified as housekeeping genes (See, Table 1). Most of these genes have never before been specifically identified as belonging in this category. This information is useful for establishing average normal expression levels and will be useful as a reference in studies of normal expression variation. In one aspect of the invention, the maintenance genes described are used to establish average normal expression levels. In some embodiments, the expression of at least one of the genes listed in table 1, preferably at least two of the genes listed in table 1, more preferably at least 10 of the genes listed in table 1, and even more preferably at least 100 of the genes listed in table 1 is monitored along with the expression of a target gene (gene of interest).

The change of the level of expression of the target gene will be evaluated using the expression of the maintenance gene(s) as a control.

Example Identification of Maintenance Genes

Methods

Sample preparation

All samples were prepared from pools of human adult poly(A) RNA purchased from Clontech (Palo Alto, Calif.). The tissues screened are listed followed by the number of tissues pooled and the Clontech catalog number in parenthesis. Heart, 3 (6533-1), brain, 5 (6516-1), lung, 5 (6524-1), kidney, 8 (6538-1), pancreas, 10 (6539-1), uterus, 10 (6537-1), testis, 19 (6535-1). Poly(A) RNA was amplified and labeled with biotin following the procedure described by Wodicka et al., 1997[32]. First strand cDNA synthesis was carried out at 37° C. for 60 minutes. The amplified cRNA (target) was purified on an affinity resin (RNeasy, Qiagen) and quantitated.

Fragmentation, array hybridization and scanning

Labeled target was fragmented by incubation at 94° C. for 35 minutes in the presence of 40 mM Tris-acetate pH 8.1, 100 mM potassium acetate, and 30 mM magnesium acetate. The hybridization solution consisted of 20 ug fragmented cRNA, 0.1 mg/ml sonicated herring sperm DNA in buffer containing 100 mM MES, 1 m[Na$^+$], 20 mMEDTA, 0.01% Tween 20 (MES). The hybridization mixture was heated to 99° C. for 5 min. followed by incubation at 45° C. for 5 min. before injection of the sample into the probe array cartridge. All hybridizations were performed in duplicate and were carried out at 45° C. for 16–17 hr with mixing on a rotisserie at 60 rpm. Following hybridization, the solutions were removed, arrays were rinsed with 1X MES (100 mM MES, 1 m[Na$^+$], 20 mMEDTA, 0.01% Tween 20). Subsequent washing and staining of the arrays was carried out using the GeneChip® fluidics station protocol EukGE_WS2. The EukGE_WS2 protocol included two post hybridization washes, staining, and a post stain wash. The first wash consisted of 10 cycles of 2 mixes per cycle with Non Stringent Wash Buffer (6X SSPE, 0.01% Tween20, 0.005% Antifoam) at 25° C. The second wash consisted of 4 cycles of 15 mixes per cycle with Stringent Wash Buffer (100 mm MES, 0.1M [Na$^+$], 0.01% Tween 20) at 50° C. The probe arrays were stained for 10 minutes in streptavidin-phycoerythrin solution (SAPE) (1X MES solution, 0.005% antifoam, 10 μg/ml SAPE (Molecular Probes, Eugene, Oreg.) 2 μg/μl acetylated BSA (Sigma, St. Louis, Mo.) at 25° C. The post stain wash consisted of 10 cycles of 4 mixes per cycle at 25° C. The probe arrays were treated for 10 minutes in antibody solution (1X MES solution, 0.005% antifoam, 2 μg/μl acetylated BSA, 0.1 μg/μl normal goat IgG (Sigma Chemical, St. Louis Mo.), 3 μg/μl antibody (goat), antistreptavidin, biotinylated (Vector Laboratories, Burlingame, Calif.) at 25° C. The final wash consisted of 15 cycles of 4 mixes per cycle at 30° C. Following washing and staining, probe arrays were scanned 2 times (multiple image scan) at 3 μm resolution using the GeneChip® System confocal scanner made for Affymetrix Inc. by Hewlett Packard.

Probe arrays

The arrays were synthesized using light-directed combinatorial chemistry as described previously. The Hu6.8K_all GeneChip® probe arrays used for the current study contain probe sets representing 7129 genes. The oligonucleotides are 25 bases in length. Probes are complementary and correspond to human genes registered in Unigene, GenBank and The Institute for Genomic Research Database (TIGR). Each probe set has oligonucleotides that are identical to sequence in the gene and oligonucleotides that contain a homomeric (base transversion) mismatch at the central base position of the oligomer used for measuring cross hybridization. Probes are selected with a bias toward the 3' region of each gene. Probe pairs representing human genes such as GAPDH, B-actin, transferrin receptor and transcription factor ISGF-3 serve as internal controls for monitoring RNA integrity. In addition, the probe arrays contain oligonucleotides representing sequences of bacterial genes, BioB, BioC, BioD, and one phage gene, Cre, as quantitative standards. Copy numbers are determined by correlating the known concentrations of the spiked standards with their hybridization. Copies per cell are calculated based on the assumption that the average transcript length is 1 kb and there are 300,000 transcripts per cell.

Analysis

All samples were hybridized in duplicate and only those transcripts detected as present in duplicate hybridizations or absent in duplicate hybridizations are reported. Of the transcripts present in duplicate hybridizations the hybridization values were within two fold. The values from the duplicate hybridizations were averaged. GeneChip® 3.0 software was used to scan and analyze the data. Microsoft Excel and Microsoft Access were also used for data analysis.

Result

Using GeneChip® probe arrays (Affymetrix, Santa Clara, Calif.), 695 genes that are expressed in common among heart, brain, lung, kidney, pancreas, uterus and testis were identified. 241 of the genes were detected at similar levels in each of the tissues; 44 genes were detected at low abundance, 72 detected at low-moderate abundance, 100 at moderate abundance, 13 at moderate-high abundance, and 12 at high abundance (See Table 1).

TABLE 1

Maintenance genes sorted by function. Abundance levels are binned by copies per cell where low, L, < 5, low-moderate,LM > 5 < 10, moderate, M, > 10 < 50, moderate-high, MH, > 50 < 100, high, H, > 100.

| Accession Number | Description | Abundance |
|---|---|---|
| M37104 | mitochondrial ATPase coupling factor 6 subunit (ATP5A) | M |
| U51478 | sodium/potassium-transporting ATPase beta-3 subunit | M |
| Z71460 | vacuolar-type H(+)-ATPase 115 kDa subunit | LM |
| D31846 | aquaporin-2 water channel | M |
| L08666 | porin (por) | M |
| AC002115 | COX6B (COXG) on chromosome 19 cosmids | M |
| M22760 | nuclear-encoded mitochondrial cytochrome c oxidase Va subunit | M |
| L32977 | ubiquinol cytochrome c reductase Rieske iron-sulphur protein | M |
| X13238 | cytochrome c oxidase subunit VIc | M |
| X16560 | COX VIIc subunit VIIc of cytochrome c oxidase | M |
| M28713 | NADH-cytochrome b5 reductase (b5R) | LM |
| D90086 | pyruvate dehydrogenase (EC 1.2.4.1) beta subunit | M |

TABLE 1-continued

Maintenance genes sorted by function. Abundance levels are binned by copies per cell where low, L, < 5, low-moderate, LM > 5 < 10, moderate, M, > 10 < 50, moderate-high, MH, > 50 < 100, high, H, > 100.

| Accession Number | Description | Abundance |
|---|---|---|
| D43682 | very-long-chain acrl-CoA dehydrogenase (VLCAD) | M |
| U17886 | succinate dehydrogenase iron-protein subunit (sdhB) | LM |
| U05861 | hepatic dihydrodiol dehydrogenase | L |
| L13761 | dihydrolipoamide dehydrogenase | L |
| J03827 | Y box binding protein-1 (YB-1) | MH |
| M26730 | mitochondrial ubiquinone-binding protein with an LTR-like sequence | M |
| X75593 | rab 13 | M |
| U79528 | SR31747 binding protein 1 | M |
| L37368 | RNA-binding protein | M |
| U33821 | tax1-binding protein TXBP151 | M |
| Z29505 | nucleic acid binding protein sub2.3 | M |
| U07857 | 18 kDa Alu RNA binding protein, | M |
| M94556 | mitochondrial specific single stranded DNA binding protein N31 | LM |
| M28209 | GTP-binding protein (RAB1) | LM |
| D13988 | rab GDI | LM |
| U51334 | putative RNA binding protein (RBP56), | LM |
| D43951 | KIAA0099, (pumilio-like, putative DNA binding) | LM |
| U65928 | Jun activation domain binding protein | L |
| X71129 | electron transfer flavoprotein beta subunit | M |
| J04058 | electron transfer flavoprotein alpha-subunit | L |
| U20285 | Gps1 (GPS1) | M |
| U45982 | G protein-coupled receptor GPR-9-6 | LM |
| U31384 | G protein gamma-11 subunit | LM |
| X81625 | CII protein | L |
| D32129 | HLA class-I (HLA-A26) heavy chain | M |
| X03100 | HLA-SB alpha (class II antigen) | M |
| X75091 | HLA-DR associated protein II (PHAPII) | L |
| J04988 | 90 kD heat shock protein | MH |
| L15189 | mitochondrial HSP75 | LM |
| M11353 | H3.3 histone class C | MH |
| U50079 | histone deacetylase HD1 | LM |
| X05855 | histone H3.3 | L |
| X57351 | 1-8D from interferon-inducible family | H |
| X59892 | IFN-inducible gamma-2 protein | M |
| J00212 | leukocyte interferon (ifn-alpha) alpha-f | L |
| M14676 | src-like kinase (slk) | M |
| L08835 | DM kinase (myotonic dystrophy kinase) | M |
| M30448 | casein kinase II beta subunit | LM |
| AJ000099 | lysosomal hyaluronidase | M |
| U91932 | AP-3 complex sigma3A subunit | M |
| M15182 | beta-glucuronidase (lysosomal enzyme) | LM |
| M29877 | alpha-L-fucosidase, (lysosomal enzyme) | LM |
| D29963 | SFA-1, a member of transmembrane 4 superfamily | M |
| L10284 | IP90, integral membrane protein, calnexin | M |
| U57877 | nuclear-encoded mitochondrial integral membrane protein CII-3 | LM |
| D78361 | ornithine decarboxylase antizyme | H |
| M33764 | ornithine decarboxylase amino acid metabolism | M |
| HG2279-HT2375 | Triosephosphate Isomerase | M |
| U86070 | phosphomannomutase (carbohydrate metabolism) | LM |
| U32114 | caveolin-2 (lipid metabolism) | L |
| Z70759 | mitochondrial 16S rRNA | H |
| M22538 | nuclear-encoded mitochondrial NADH-ubiquinone reductase 24kD subunit | M |
| M22760 | nuclear-encoded mitochondrial cytochrome c oxidase Va subunit | M |
| X60036 | mitochondrial phosphate carrier protein | M |
| M37104 | mitochondrial ATPase coupling factor 6 subunit (ATP5A) | M |
| M26730 | mitochondrial ubiquinone-binding protein with an LTR-like sequence | M |
| X99728 | NDUFV3, mitochondrial NADH ubiquinone oxidoreductase | M |
| U59309 | nuclear-encoded mitochondrial fumarase precursor (FH) | LM |
| L15189 | mitochondrial HSP75 | LM |
| M94556 | mitochondrial specific single stranded DNA binding protein, | LM |
| U57877 | nuclear-encoded mitochondrial integral membrane protein CII-3 | LM |
| L07033 | hydroxymethylglutaryl-CoA lyase | LM |
| U15174 | Nip3 (NIP3) (mitochondrial, pro-apoptotic protein family) | L |
| U45975 | phosphatidylinositol (4,5) bisphosphate 5-phosphatase homolog | M |
| X74008 | phosphatase 1 gamma | LM |
| X81003 | HCG V (phosphatase inhibitor) | LM |
| M65254 | phosphatase 2A 65 kDa regulatory subunit-beta | L |
| Z27113 | RNA polymerase II subunit 14.4 kD | M |
| U37690 | RNA polymerase II subunit (hsRPB10) | M |
| Z47727 | RNA polymerase II subunit | LM |
| L02426 | 26S protease (S4) regulatory subunit | M |
| M23254 | Ca2-activated neutral protease large subunit (CANP) | M |
| X12451 | pro-cathepsin L (major excreted protein MEP) | M |
| S69272 | cytoplasmic antiproteinase, 38kD intracellular serine proteinase inhibitor | M |
| D29012 | proteasome subunit Y | M |
| D26598 | proteasome subunit HsC10-II | M |
| D26599 | proteasome subunit HsC7-I | M |
| D38047 | 26S proteasome subunit p31 | M |
| AB003177 | proteasome subunit p27 | LM |
| D00763 | proteasome subunit HC9 | LM |
| D50063 | proteasome subunit p40_/Mov34 protein, | LM |
| X61970 | macropain subunit zeta (proteasome) | LM |
| X95586 | MB1 | LM |
| D00760 | proteasome subunit HC3 | L |
| D00762 | proteasome subunit HC8 | L |
| M63959 | alpha-2-macroglobulin receptor-associated protein | M |
| D23673 | insulin receptor substrate-1-like (IRS-1) | M |
| X07979 | fibronectin receptor beta subunit | M |
| U83239 | CC chemokine STCP-1 (immune function, T-receptor assoc) | M |
| M88279 | immunophilin (FKBP52) | M |
| U45982 | G protein-coupled receptor GPR-9-6 | LM |
| X56253 | MPR46 46kd mannose 6-phosphate receptor | LM |
| X80763 | 5-HT2c receptor | LM |
| L40357 | thyroid receptor interactor (TRIP7) | L |
| M22538 | nuclear-encoded mitochondrial NADH-ubiquinone reductase 24kD subunit | M |
| X91247 | thioredoxin reductase | LM |
| X15414 | aldose reductase (EC 1.1.1.2) | LM |
| M28713 | NADH-cytochrome b5 reductase (b5R) | LM |
| U07418 | DNA mismatch repair (hmlh1) | L |
| U49785 | D-dopachrome tautomerase | LM |
| J05249 | replication protein A 32-kD subunit | LM |
| HG3076-HT3238 | heterogeneous nuclear ribonucleoprotein K, alt.splice 1 | M |
| X16135 | novel heterogeneous nuclear RNP protein, L protein | M |
| X78136 | hnRNP-E2 | M |
| M94630 | hnRNP-C like protein | M |
| M16342 | nuclear ribonucleoprotein particle (hnRNP) C protein | LM |
| Z23064 | hnRNP G protein | L |
| X81625 | ribosomal protein L37a (RPL37A) | H |
| Z12962 | homologue to yeast ribosomal protein L41 | H |
| HG3214-HT3391 | Metallopanstimulin, MPS-1 (S27, Zinc finger) | H |
| HG1800-HT1823 | ribosomal protein S20 | H |
| U14973 | ribosomal protein S29 | H |
| Z26876 | ribosomal protein L38 | MH |
| M77232 | ribosomal protein S6 | MH |
| HG821-HT821 | ribosomal protein S13 | MH |
| M13934 | RPS14, ribosomal protein S14 | MH |
| M84332 | ADP-ribosylation factor 1 | M |

TABLE 1-continued

Maintenance genes sorted by function. Abundance levels are binned by copies per cell where low, L, < 5, low-moderate,LM > 5 < 10, moderate, M, > 10 < 50, moderate-high, MH, > 50 < 100, high, H, > 100.

| Accession Number | Description | Abundance |
|---|---|---|
| M36341 | ADP-ribosylation factor 4 (ARF4) | LM |
| D49396 | Apol (MER5-like protein) | L |
| U57341 | neurofilament triplet L protein | MH |
| Z19554 | vimentin | MH |
| X51521 | ezrin | M |
| HG2238-HT2321 | nuclear mitotic apparatus protein 1, alt.splice form 2 | M |
| M64571 | microtubule-associated protein 4 | M |
| M31013 | nonmuscle myosin heavy chain (NMHC) | M |
| V00599 | fragment encoding beta-tubulin (D-beta-1) | M |
| U24105 | coatomer protein (HEPCOP) , | M |
| M95627 | angio-associated migratory cell protein (AAMP) | LM |
| D38549 | KIAA0068 | LM |
| U56637 | capping protein alpha subunit isoform I | LM |
| X72964 | caltractin | LM |
| X70476 | subunit of coatomer complex | LM |
| D28915 | hepatitis C-associated microtubular aggregate protein p44 | L |
| X82103 | beta-COP | L |
| D14710 | ATP synthase alpha subunit | MH |
| X76013 | QRSHs, glutaminyl-tRNA synthetase | M |
| X83218 | ATP synthase | M |
| X60221 | H+-ATP synthase subunit b | M |
| D31890 | KIAA0070 | M |
| U09510 | glycyl-tRNA synthetase | LM |
| U79262 | deoxyhypusine synthase | LM |
| J03473 | poly(ADP-ribose) synthetase | LM |
| X94754 | yeast methionyl-tRNA synthetase homologue | LM |
| L49380 | transcription factor ZFM1 | M |
| U95040 | transcriptional corepressor hKAP1/TIF1B | M |
| U10323 | nuclear factor NF45 | M |
| L12168 | adenylyl cyclase-associated protein (CAP) , | M |
| M97935 | transcription factor ISGF-3 sequence | LM |
| X52882 | t-complex polypeptide 1 | LM |
| L19067 | NF-kappa-B transcription factor p65 subunit | L |
| D63478 | KIAA0144 | L |
| U15782 | cleavage stimulation factor 77kDa subunit (polyadenylation) | L |
| L20298 | transcription factor (CBFB) | L |
| U56417 | lysophosphatidic acid acyltransferase-alpha | M |
| U62739 | branched-chain amino acid aminotransferase (ECA40) | M |
| Y08200 | rab geranylgeranyl transferase, alpha-subunit | M |
| U82010 | heme A: farnesyltransferase (COX10) | LM |
| U86529 | glutathione transferase Zeta 1 (GSTZ1) | LM |
| D26535 | dihydrolipoamide succinyltransferase | L |
| U50523 | BRCA2 region | M |
| U57342 | myelodysplasia/myeloid leukemia factor 2 (MLF2) , | M |
| HG4541-HT4946 | transformation-related protein | M |
| M15990 | c-yes-1 | L |
| L12535 | RSU-1/RSP-1 (Ras suppressor) | L |
| J04169 | elongation factor EF-1 alpha | H |
| X51466 | elongation factor 2 | MH |
| L26247 | sui1,N278 iso1 | MH |
| U46025 | translation initiation factor eIF-3 p110 subunit | M |
| X55733 | initiation factor 4B | LM |
| X98743 | RNA helicase (Myc-regulated dead box protein) | L |
| U36341 | SLC6A8 (creatine transporter) | M |
| U51478 | sodium/potassium-transporting ATPase beta-3 subunit | M |
| X81817 | BAP31 (ER, protein sorting) | M |
| Y00281 | ribophorin I (ER) | M |
| Y00282 | ribophorin II (ER) | M |
| U70660 | copper transport protein HAH1 | LM |
| U41740 | trans-Golgi p230 | LM |
| X12791 | signal recognition particle,SRP 19kD protein (ER) | L |
| X56997 | UbA52 coding for ubiquitin-52 amino acid fusion protein | MH |
| M26880 | ubiquitin | M |
| U46751 | phosphotyrosine independent ligand p62 for the Lck SH2 domain | M |
| U39317 | E2 ubiquitin conjugating enzyme UbcH5B (UBCH5B) , | L |
| HG3214-HT3391 | Metallopanstimulin , MPS-1 (S27, Zinc finger) | H |
| X70394 | OZF | L |
| U09412 | zinc finger protein ZNF134 | L |
| HG3454-HT3647 | zinc finger protein 20 | L |
| X67698 | unknown product | M |
| L11066 | unknown product | M |
| U79294 | unknown product | M |
| D28124 | unknown product | M |
| D21261 | KIAA0120 | M |
| D87451 | KIAA0262 | M |
| D14694 | KIAA0024 | M |
| ISGF3A/M97935 | unknown product | LM |
| L20773 | unknown product | LM |
| D42043 | KIAA0084 | LM |
| D50911 | KIAA0121 | LM |
| D79994 | KIAA0172 | LM |
| D29643 | KIAA0115 | LM |
| D14662 | KIAA0106 | LM |
| D86963 | KIAA0208 | LM |
| D21853 | KIAA0111 | LM |
| D63476 | KIAA0142 | LM |
| D42087 | KIAA0118 | L |
| D30756 | KIAA0049 | L |
| D80004 | KIAA0182 | L |
| D79993 | KIAA0171 | L |
| L40395 | unknown product | L |
| | Others | |
| X98482 | TNNT2, (troponin) | H |
| U06155 | chromosome 1q subtelomeric sequence | H |
| M33680 | 26-kDa cell surface protein TAPA-1 | H |
| M13450 | esterase D | M |
| U11861 | G10 homolog, edg-2 | M |
| U62317 | hypothetical protein 384D8_2 on chromosome 22q13 (other) | M |
| HG3991-HT4261 | Cpg-enriched DNA (other) | M |
| X80199 | MLN51 | M |
| X80200 | MLN62 | M |
| U46570 | tetratricopeptide repeat protein (tpr1) N297 (other) | M |
| HG3597-HT3800 | major histocompatibility complex, class I | M |
| X71428 | fus (nuclear RNA binding protein) | M |
| U73824 | p97 | M |
| Y00433 | glutathione peroxidase (peroxide clearance) | M |
| U02493 | 54 kDa protein | M |
| U88964 | HEM45 | LM |
| D78129 | squalene epoxidase (sterol biosynthesis) | LM |
| D43951 | KIAA0099, (pumilio-like, putative DNA binding) | LM |
| X96484 | DGCR6 protein (organization, migration during development) | LM |
| HG1155-HT4822 | colony-stimulating factor 1, macrophage, alt. splice 3 | LM |
| L38932 | GT197 N305 | LM |
| X66379 | tpr | LM |
| L42572 | p87/89 (ER transmembrane protein) | LM |
| X80695 | OXA1Hs (cytochrome oxidase assembly) | LM |
| Y00097 | p68 (membrane associated, calcium binding protein) | LM |
| Z48042 | GPI-anchored protein p137 | LM |
| Z35093 | SURF-1 (Surfeit gene family, biogenesis of cytochrome C oxidase) | LM |

TABLE 1-continued

Maintenance genes sorted by function. Abundance levels are binned by copies per cell where low, L, < 5, low-moderate, LM > 5 < 10, moderate, M, > 10 < 50, moderate-high, MH, > 50 < 100, high, H, > 100.

| Accession Number | Description | Abundance |
|---|---|---|
| U54644 | tub homolog | LM |
| Z93784 | mouse brain protein E46-like sequence | L |
| L38616 | brain and reproductive organ-expressed protein (BRE) | L |
| D63506 | unc-18 homologue | L |
| U18009 | human gene chromosome 17q21 | L |
| L27476 | X104 (membrane associated, kinase containing protein family) | L |
| M73720 | mast cell carboxypeptidase A (MC-CPA) | L |

For example, no difference in expression level was detected for 5 of the genes and a two-fold difference was detected for 46 of the genes. 454 genes are expressed in all seven tissues but vary in expression level by more than fourfold. 333 of the genes vary in expression level by 5-10 fold. Included in this subset are genes frequently used as controls in standard expression analysis including beta actin (M10277) varying by 7-fold with highest expression in brain and uterus and lowest expression in heart, and GAPDH (M33197) varying by 8-fold with highest expression in brain, heart and kidney and lowest in pancreas. Another form of beta actin (X00351) varied by 22-fold with highest expression in uterus and lowest in pancreas. Alpha actin (X13839) varied by 23-fold and gamma actin (M19283) by 9-fold. 40 genes expressed in all seven tissues differ in transcript levels by greater than 19 fold and of these eight differ by more than 50-fold, including COX7A muscle isoform (M83186) varying by 52-fold, highest in heart, lowest in kidney, pancreas and testis, lectin (J04456) varying by 58-fold, highest in uterus, lowest in kidney and pancreas, myosin heavy chain (AF001548) varying by 61-fold, highest in uterus, lowest in brain and pancreas, elongation factor-1 delta (Z21507) varying by 69-fold, highest in pancreas, lowest in lung and kidney, RNA polymerase II elongation protein (Z47087) varying by 70-fold, highest in brain, lowest in pancreas, extracellular mRNA for glutathione peroxidase (D00632) varying by 78-fold, highest in kidney, lowest in brain, pancreas and testis, 14-9-9 protein eta chain (D78577) varying by 81-fold, highest in brain, lowest in testis, and L-arginie:glycine amidinotransferase (S68805) varying by 133-fold, highest in pancreas and lowest in heart and lung.

In the same experiments, genes expressed uniquely in each of the seven tissues were also identified (Table II). For instance, in heart there were 4 transcripts not detected in the other 6 tissues; muscle glycogen synthase (J04501), NADH oxidoreductase subunit (L04490), MLC-IV/Sb isoform (M24248) and cytokine inducible nuclear protein (X83703). Twenty nine uniquely expressed transcripts were identified in the kidney including many that are expected such as potassium channel ROM-K3 (U65406) and renal Na/Pi cotransporter (L13258) as well as genes of unknown function such as a gene that maps to chromosome 19 (U95090). 45 uniquely expressed transcripts were detected in uterus, 28 in pancreas and 19 in lung. Not surprisingly, the greatest number of uniquely expressed genes, 91 and 94 respectively, were found in brain and testis.

TABLE II

Genes Uniquely Expressed in a Comparison of Eleven Human Tissues

| Accession No. | Description | Bin* |
|---|---|---|
| *Uniquely Expressed in Adult Heart* | | |
| J04501 | Muscle glycogen synthase | M |
| M24248 | MLC-1V/Sb isoform | M |
| X83703 | Cytokine inducible nuclear protein | LM |
| *Uniquely Expressed in Fetal Kidney* | | |
| D88532 | P55pik | L |
| M26901 | Renin | M |
| M81829 | Somatostatin receptor isoform 1 | L |
| U19107 | ZNF127 | L |
| U19906 | Arginine vasopressin receptor 1 (AVPR1) | L |
| U34301 | Nonmuscle myosin heavy chain IIB | LM |
| X58431 | HOX 2.2 | M |
| Z67743 | CLC-7 chloride channel protein | LM |
| *Uniquely Expressed in Fetal Liver* | | |
| AF000573 | Homogentisate 1,2-dioxygenase | LM |
| D00097 | Amyloid P component (SAP) | M |
| D16611 | Coproporphyrinogen oxidase | M |
| D16626 | Histidase | M |
| D21063 | KIAA0030 | M |
| D26361 | KIAA0042 | L |
| D38535 | PK-120 | H |
| D38537 | Protoporphyrinogen oxidase | M |
| D42055 | KIAA0093 | L |
| D49357 | S-adenosylmethionine synthetase | LM |
| D49742 | HGF activator like protein | M |
| D79988 | KIAA0166 | L |
| D84454 | UDP-galactose translocator | LM |
| D87116 | MAP kinase kinase 3b | M |
| D90282 | Carbamyl phosphate synthetase 1 (EC 6.3.4.16) | MH |
| HG1148-HT1148 | Lipopolysaccharide-Binding Protein | H |
| HG1227-HT1227 | Collagen, Type II, Alpha 1 | M |
| HG1649-HT1652 | Elastase 1 | M |
| HG2730-HT2827 | Fibrinogen, A Alpha Polypeptide, Alt. Splice 2, E | H |
| HG3105-HT3281 | Atpase, Cu2+ Transporting | L |
| HG3565-HT3768 | Zinc Finger Protein | M |
| HG627-HT5097 | Rhesus (Rh) Blood Group System Ce-Antigen, Alt. Splice 2, Rhvi | MH |
| J00116 | Collagen COL2A1 | M |
| J02982 | Glycophorin B | MH |
| J03474 | Serum amyloid A | H |
| J03626 | UMPS | L |
| J05070 | Type IV collagenase | L |
| J05500 | Beta-spectrin (SPTB) | M |
| K01383 | Metallothionein-I-A | MH |
| K02402 | Coagulation factor IX | M |
| L00190 | Antithrombin III (ATAIII) | H |
| L01664 | Eosinophil Charcot-Leyden crystal (CLC) protein (lysophospholipase) | L |
| L06133 | Putative Cu++-transporting P-type ATPase | L |
| L09708 | Complement component 2 (C2), allele b | MH |
| L11244 | C4-binding protein beta-chain | M |
| L31860 | Glycophorin A, MN-types (GYPA) | M |
| L32140 | Afamin | M |
| L34081 | Bile acid CoA: Amino acid N-acyltransferase | LM |
| L48516 | Paraoxonase 3 (PON3) | M |
| L76571 | Nuclear hormone receptor (shp) | M |
| L77567 | Mitochondrial citrate transport protein (CTP) | M |
| M10014 | Fibrinogen gamma chain and gamma-prime chain | H |
| M10058 | Asialoglycoprotein receptor H1 | M |
| M10950 | Alpha-fetoprotein (AFP) | M |
| M11025 | Asialoglycoprotein receptor H2 | M |
| M11567 | Angiogenin and three Alu repetitive sequences | M |
| M13699 | Ceruloplasmin (ferroxidase) | MH |
| M14091 | Thyroxine-binding globulin | M |

TABLE II-continued
Genes Uniquely Expressed in a Comparison of Eleven Human Tissues

| Accession No. | Description | Bin* |
|---|---|---|
| M15205 | Thymidine kinase with clustered Alu repeats in the introns | M |
| M16961 | Alpha-2-HS-glycoprotein alpha and beta chain | H |
| M16967 | Coagulation factor V | M |
| M16973 | Complement protein C8 beta subunit | M |
| M17262 | Prothrombin (F2) gene, and Alu and KpnI repeats | H |
| M19481 | Follistatin | LM |
| M19828 | Apolipoprotein B-100 (apoB) | H |
| M20786 | Alpha-2-plasmin inhibitor | MH |
| M22638 | LYL-1 protein | M |
| M22898 | Phosphoprotein p53 | L |
| M27819 | Anion exchange protein 1 (AE1, band 3) | MH |
| M29194 | Triglyceride lipase | M |
| M36803 | Hemopexin | H |
| M58569 | Fibrinogen alpha-subunit bipartite transcript of extended (alpha-E) variant | H |
| M58600 | Heparin cofactor II (HCF2), exons 1 through 5 | H |
| M59820 | Granulocyte colony-stimulating factor receptor (CSF3R) | LM |
| M60298 | Erythrocyte membrane protein band 4.2 (EPB42) | MH |
| M61827 | Leukosialin (CD43) | LM |
| M61855 | Cytochrome P4502C9 (CYP2C9), clone 25 | L |
| M64554 | F13A1 gene (coagulation factor XIIIb) | M |
| M68895 | Alcohol dehydrogenase 6 | L |
| M71243 | Glycophorin Sta (type A) exons 3 and 4 | MH |
| M75106 | Prepro-plasma carboxypeptidase B | MH |
| M86873 | Type A plasminogen related | M |
| S42457 | Photoreceptor cGMP-gated channel | L |
| S48983 | SAA4, serum amyloid A | M |
| S70004 | Glycogen synthase | LM |
| S72370 | Pyruvate carboxylase | LM |
| S77393 | Transcript ch138 | LM |
| S77763 | Nuclear factor erythroid 2 | M |
| S77893 | Glycophorin SAT | MH |
| S78234 | Nuc2 homolog | LM |
| U00001 | Homologue of S. pombe nuc2+ and A. nidulans bimA | L |
| U01317 | Epsilon-globin | LM |
| U05255 | Glycophorin HeP2 | H |
| U08006 | Complement 8 alpha subunit (C8A) | M |
| U12778 | Acyl-CoA dehydrogenase | LM |
| U13061 | Dehydroepiandrosterone sulfotransferase (STD) | L |
| U14518 | Centromere protein-A (CENP-A) | L |
| U18919 | Clone pOV-2 | L |
| U20530 | Bone phosphoprotein spp-24 precursor | M |
| U20979 | Chromatin assembly factor-I p150 subunit | L |
| U32989 | Tryptophan oxygenase (TDO) | M |
| U61836 | Putative cyclin G1 interacting protein | M |
| U65404 | Erythroid-specific transcription factor EKLF | M |
| U72515 | C3f | M |
| U73167 | H_LUCA14.2a | M |
| U73524 | Putative ATP/GTP-binding protein (HEAB) | L |
| U90544 | Sodium phosphate transporter (NPT3) | M |
| V01514 | Alpha-fetoprotein (AFP) | H |
| X02176 | Complement component C9 | M |
| X02544 | Alpha1-acid glycoprotein (orosomucoid) | H |
| X03473 | Histone H1(0) | M |
| X04898 | Apolipoprotein | H |
| X05309 | C3b/C4b receptor (CR1) F allotype | L |
| X06482 | Theta 1-globin | M |
| X06562 | Growth hormone receptor | L |
| X13293 | B-myb | M |
| X13589 | Aromatase (estrogen synthetase) | LM |
| X14329 | Carboxypeptidase N small subunit (EC 3.4.17.3) | LM |
| X14690 | Plasma inter-alpha-trypsin inhibitor heavy chain H(3) | H |
| X15422 | Mannose-binding protein C | M |
| X16260 | Inter-alpha-trypsin inhibitor subunit 3 | H |
| X16983 | Integrin alpha-4 subunit | L |
| X17059 | NAT1 gene for arylamine N-acetyltransferase | L |
| X17254 | Transcription factor Eryf1 | M |
| X51688 | Cyclin A | LM |
| X53414 | Peroxisomal L-alanine:glyoxylate aminotransferase | MH |
| X55668 | Proteinase 3 | M |
| X56692 | C-reactive protein | M |
| X56741 | Rab8 | L |
| X58199 | Beta adducin | M |
| X59618 | RR2 small subunit ribonucleotide reductase | LM |
| X59711 | CAAT-box DNA binding protein subunit A | L |
| X59812 | CYP 27 vitamin D3 25-hydroxylase | M |
| X62822 | Beta-galactoside alpha-2,6-sialyltransferase | LM |
| X63097 | Rhesus polypeptide (RhXIII) | L |
| X64594 | Erythrocyte plasma membrane glycoprotein | MH |
| X64877 | Serum protein | LM |
| X65550 | Antigen of monoclonal antibody Ki-67 | L |
| X74330 | DNA primase (subunit p48) | L |
| X75315 | Seb4B | M |
| X77737 | Red cell anion exchanger (EPB3, AE1, Band 3) | H |
| X80907 | P85 beta subunit of phosphatidyl-inositol-3-kinase | M |
| X91148 | Microsomal triglyceride transfer protein | LM |
| X98337 | Complement factor H-related protein 4 | M |
| Y00317 | Liver microsomal UDP-glucuronosyltransferase (UDPGT) | LM |
| Z15005 | CENP-E | LM |
| Z26248 | Eosinophil granule major basic protein | LM |
| Z28339 | Delta 4-3-oxosteroid 5 beta-reductase | LM |
| Z32684 | XK membrane transport protein | M |
| Z83821 | DNA sequence from PAC 296K21 on chromosome X contains cytokeratin exon, delta-aminolevulinate synthase (erythroid); 5-aminolevulinic acid synthase | H |
| Z84721 | DNA sequence from cosmid GG1 from a contig from the tip of the short arm of chromosome 16, spanning 2Mb of 16p13.3 | H |
| *Uniquely Expressed in Fetal Lung* | | |
| D87071 | KIAA0233 | LM |
| HG4638-HT5050 | Spliceosomal Protein Sap 49 | L |
| U18671 | Stat2 | L |
| U40434 | Mesothelin or CAK1 antigen precursor | LM |
| X52896 | Dermal fibroblast elastin | M |
| X97748 | PTX3 | LM |
| *Uniquely Expressed in Adult Brain* | | |
| D87463 | KIAA0273 | M |
| HG2259-HT2348 | Tubulin, Alpha 1, Isoform 44 | M |
| HG3437-HT3628 | Myelin Proteolipid Protein, Alt. Splice 2 | H |
| L00354 | Cholecystokinin (CCK) | M |
| L76224 | NMDA receptor | M |
| L76627 | Metabotropic glutamate receptor 1 alpha (mGluR1alpha) | L |
| M55267 | EV12 protein | LM |
| M59488 | S100 protein beta-subunit | M |
| S50017 | 2',3'-cyclic nucleotide 3'-phosphodiesterase | M |
| S69965 | Beta-synuclein | M |
| U01824 | Glutamate/aspartate transporter II | M |
| U06698 | Neuronal kinesin heavy chain | LM |
| U27768 | RGP4 | M |
| U62801 | Protease M | M |
| U82532 | GDI-dissociation inhibitor RhoGDIgammma | LM |
| X59065 | FGF, exon 3 | M |
| X64810 | PC1/PC3 | LM |
| X73882 | E-MAP-115 | LM |
| X99076 | NRGN, exons 2, 3 & 4 (joined CDS) | H |
| Z48051 | Myelin oligodendrocyte glycoprotein (MOG) | M |
| *Uniquely Expressed in Adult Kidney* | | |
| J04093 | Phenol UDP-glucuronosyltransferase (UDPGT) | LM |
| L13258 | Renal Na/Pi-cotransporter | M |
| M19878 | Calbindin 27, exons 1 and 2, and Alu repeat | M |
| S77576 | ERV9 reverse transcriptase homolog (clone RTI8) | L |
| U17418 | Hormone/parathyroid hormone-related peptide receptor | M |
| X13227 | D-amino acid oxidase | M |
| X60708 | PcHDP7, liver dipeptidyl peptidase IV | L |

TABLE II-continued

Genes Uniquely Expressed in a Comparison of Eleven Human Tissues

| Accession No. | Description | Bin* |
|---|---|---|
| | Uniquely Expressed in Adult Uterus | |
| D21337 | Collagen | L |
| D86961 | KIAA0206 | L |
| HG721-HT4828 | Placental Protein 14, Endometrial Alpha 2 Globulin, Alt. Splice 3 | M |
| L00205 | K6b (epidermal keratin, type II) | L |
| L02785 | Colon mucosa-associated (DRA) | L |
| L06419 | Lysyl hydroxylase (PLOD) | LM |
| L08044 | Intestinal trefoil factor | LM |
| L10343 | Elafin | M |
| L14848 | MHC class I-related protein | L |
| M19888 | Small proline rich protein (sprI) | M |
| M21121 | T cell-specific protein (RANTES) | L |
| M21389 | Keratin type II (58 kD) | M |
| M55543 | Guanylate binding protein isoform II (GBP-2) | L |
| M59979 | Prostaglandin endoperoxide synthase | L |
| M60284 | Neurokinin A receptor (NK-2R) | LM |
| M62783 | Alpha-N-acetylgalactosaminidase | L |
| M85276 | NKG5 | M |
| M86757 | Psoriasin | M |
| M86849 | Connexin 26 (GJB2) | L |
| M96233 | Transferase class mu number 4 (GSTM4) | LM |
| S66896 | Squamous cell carcinoma antigen, serine protease inhibitor | L |
| S72493 | Keratin 16 homolog | M |
| S81661 | Keratinocyte growth factor | L |
| U07969 | Intestinal peptide-associated transporter HPT-1 | L |
| U09278 | Fibroblast activation protein | L |
| U09584 | PL6 protein (PL6) | L |
| U11717 | Calcium activated potassium channel (hslo) | L |
| U24488 | Tenascin-X (XA) | M |
| U25138 | MaxiK potassium channel beta subunit | M |
| U37283 | Microfibril-associated glycoprotein-2 MAGP-2 | M |
| U43185 | Signal transducer and activator of transcription Stat5A | L |
| U60325 | DNA polymerase gamma, nuclear gene encoding mitochondrial protein | L |
| U76764 | CD97 | LM |
| U81523 | Endometrial bleeding associated factor | M |
| X03635 | Oestrogen receptor | M |
| X06256 | Fibronectin receptor alpha subunit | LM |
| X07695 | Cytokeratin 4 C-terminal region | M |
| X07696 | Cytokeratin 15 | L |
| X16662 | Vascular anticoagulant-beta (VAC-beta) | L |
| X54162 | 64 Kd autoantigen expressed in thyroid and extra-ocular muscle | M |
| X63629 | P cadherin | L |
| X75535 | PxF protein | L |
| X83857 | Prostaglandin E receptor (EP3a1) | L |
| X92521 | MMP-19 protein | L |
| X93510 | 37 kDa LIM domain protein | LM |
| X96719 | AICL (activation-induced C-type lectin) | LM |
| X98311 | Carcinoembryonic antigen, CGM2 | L |
| Y07755 | S100A2, exon 1, 2 and 3 | M |
| | Uniquely Expressed in Adult Testis | |
| D17570 | Zona-pellucida-binding protein (sp38). | M |
| D50925 | KIAA0135 | L |
| D64109 | Tob family | L |
| D78333 | Testis-specific TCP20 | M |
| D78334 | Ankyrin motif | MH |
| HG2075-HT2137 | Camp-Responsive Element Modulator, Alt. Splice 1 | M |
| HG36-HT4101 | Polymyositis/Scleroderma (Pm-Scl) Autoantigen, Alt. Splice 2 | L |
| HG3725-HT3981 | Insulin-Like Leydig Hormone | M |
| HG4316-HT4586 | Transketolase-Like Protein | L |
| L01042 | HIV1 tata element modulatory factor | L |
| L07515 | Heterochromatin protein homologue (HP1) | LM |
| L14754 | DNA-binding protein (SMBP2) | LM |
| L22214 | Denosine A1 receptor (ADORA1), exons 1-6 | L |
| L36861 | Guanylate cyclase activating protein (GCAP), exons 1-4 | L |
| L42324 | G protein-linked receptor (GPCR) | L |
| L76687 | Grb14 | L |
| M13981 | Inhibin A-subunit | M |
| M14565 | Cholesterol side-chain cleavage enzyme P450scc | L |
| M21539 | Small proline rich protein (sprII) | L |
| M31606 | Phosphorylase kinase (PSK-C3) | M |
| M63256 | Major Yo paraneoplastic antigen (CDR2) | L |
| M73077 | Glucocorticoid receptor repression factor 1 (GRF-1) | LM |
| M86808 | Pyruvate dehydrogenase complex (PDHA2) | L |
| M91438 | Kazal-type serine proteinase (HUSI-II) | M |
| S68134 | CREM, cyclic AMP-responsive element modulator beta isoform | LM |
| S78873 | Zn2+ binding protein/guanine nucleotide exchange factor | L |
| U03644 | Recepin | L |
| U10362 | GP36b glycoprotein | L |
| U13680 | Lactate dehydrogenase-C (LDH-C) | M |
| U15422 | Protamine 1 (PRM1), protamine 2 (PRM2) and transition protein 2 (TNP2) | H |
| U17032 | P190-B (p190-B) | L |
| U17280 | Steroidogenic acute regulatory protein (StAR) | LM |
| U19147 | GAGE-6 protein | LM |
| U20362 | Tg737 | LM |
| U22815 | LAR-interacting protein 1a | L |
| U31929 | Orphan nuclear receptor (DAX1) | L |
| U38175 | HuR RNA binding protein (HuR) | L |
| U41763 | Muscle specific clathrin heavy chain (CLTD) | L |
| U43944 | Breast cancer cytosolic NADP(+)-dependent malic enzyme | L |
| U47054 | Putative mono-ADP-ribosyltransferase (htMART) | LM |
| U58970 | Putative outer mitochondrial membrane 34 kDa Translocase hTOM34 | M |
| U60665 | Testis specific basic protein (TSBP) | L |
| U65011 | Preferentially expressed antigen of melanoma (PRAME) | LM |
| U65092 | Melanocyte-specific gene 1 (msg1) | M |
| U65533 | Regulator of nonsense transcript stability (RENT1) | L |
| U65918 | Putative RNA binding protein (DAZH) | L |
| U66726 | Testis specific RNA binding protein (SPGYLA) | LM |
| U70981 | Interleukin-13 receptor | L |
| U78722 | Zinc finger protein 165 (Zpf165) | L |
| U79266 | Clone 23627 | L |
| U84720 | Export protein Rae1 (RAE1) | LM |
| U89606 | Pyridoxal kinase | M |
| X04445 | InhA gene exon 1 (and joined CDS) | LM |
| X05246 | Testis-specific PGK-2 gene for phosphoglycerate kinase (ATP:3-phospho-D-glycerate 1-phosphotransferase, EC 2.7.2.3) | M |
| X07948 | Transition protein 1 (TP1) | H |
| X12433 | PHS1-2, ORF homologous to membrane Receptor proteins | LM |
| X14968 | RII-alpha subunit of cAMP dependent protein kinase | L |
| X68285 | Glycerol kinase | L |
| X69398 | OA3 antigenic surface determinant | L |
| X70218 | Protein phosphatase X | LM |
| X78706 | Carnitine acetyltransferase | M |
| X78711 | Glycerol kinase testis specific 1 | L |
| X78712 | Glycerol kinase testis specific 2 | M |
| X79200 | SYT-SSX, synovial sarcoma translocation junction | M |
| X89960 | Mitochondrial capsule selenoprotein | M |
| X95239 | Cysteine-rich secretory protein-2/type I | M |
| X99374 | Fertilin beta | L |
| Y00970 | Acrosin (EC 3.4.21.10) | M |
| Y12856 | AMP-activated protein kinase alpha-1 | L |
| Z22780 | Cylicin | L |
| Z46788 | Cylicin II | L |
| Z46967 | Calicin | M |
| Z48570 | Sp17 | LM |
| Z49105 | HD21 | M |
| Z50115 | Thimet oligopeptidase (metalloproteinase) | L |
| Z75190 | Apolipoprotein E receptor 2. | L |

TABLE II-continued

Genes Uniquely Expressed in a Comparison of Eleven Human Tissues

| Accession No. | Description | Bin* |
|---|---|---|
| *Uniquely Expressed in Fetal Brain* | | |
| HG1996-HT2044 | Guanine Nucleotide-Binding Protein Rap2, Ras-Oncogene Related | LM |
| HG4063-HT4333 | Transcription Factor Hbf-2 | M |
| L07919 | Homeodomain protein DLX-2 | M |
| L13744 | AF-9 | LM |
| M64358 | Rhom-3 | LM |
| M88461 | Neuropeptide Y peptide YY receptor | M |
| U00802 | Drebrin E2 (DBN1) | M |
| U04735 | Microsomal stress 70 protein ATPase core (stch) | L |
| U09413 | Zinc finger protein ZNF135 | L |
| U11701 | LIM-homeobox domain protein (hLH-2) | M |
| U35234 | Protein tyrosine phosphatase sigma | M |
| U43843 | H-neuro-d4 protein | M |
| U64871 | Putative G protein-coupled receptor (GPR19) | L |
| U66198 | Fibroblast growth factor homologous factor 2 (FHF-2) | M |
| U79247 | Clone 23599 | LM |
| U81262 | Lerk-5 (Lerk-5) | LM |
| X95425 | EHK-1 receptor tyrosine kinase | L |
| Z11933 | N-Oct 3, N-Oct5a, and N-Oct 5b proteins | M |
| Z70220 | Unknown protein (clone ICRFp507O0882) | M |
| *Uniquely Expressed in Adult Pancreas* | | |
| AF014958 | Chemokine receptor X (CKRX) | LM |
| D31797 | CD40 ligand (CD40L) | LM |
| J00268 | Insulin | H |
| J02883 | Colipase | H |
| J05125 | Triglyceride lipase | H |
| L08010 | Reg gene homologue | H |
| L14813 | Carboxyl ester lipase like protein (CELL) | MH |
| M16652 | Pancreatic elastase IIA | H |
| M16653 | Elastase IIB | H |
| M21056 | Pancreatic phospholipase A-2 (PLA-2) | H |
| M22612 | Pancreatic trypsin 1 (TRY1) | H |
| M24349 | Parathyroid hormone-like protein (PLP) | L |
| M24400 | Chymotrypsinogen | H |
| M55131 | Cystic fibrosis transmembrane conductance regulator (CFTR) | M |
| M74096 | Long chain acyl-CoA dehydrogenase (ACADL) | L |
| M81057 | Procarboxypeptidase B | H |
| M93284 | Pancreatic lipase related protein 2 (PLRP2) | H |
| S82198 | Caldecrin, serum calcium-decreasing factor | H |
| X54457 | Bile-salt-stimulated lipase (BSSL) | H |
| X67318 | Procarboxypeptidase A1 | H |
| X71877 | Chymotrypsin-like protease CTRL-1 | H |
| Y00705 | Pancreatic secretory inhibitor (expressed in neoplastic tissue) | H |
| Y08134 | ASM-like phosphodiesterase 3b | LM |

*The abundance levels in copies per cell: L < 5, LM > 5 < 10, M > 10 < 50, MH > 50 < 100, H > 100.

CONCLUSION

The present invention provides methods and compositions for identifying and using maintenance genes. It is to be understood that the above description is intended to be illustrative and not restrictive. Many variations of the invention will be apparent to those of skill in the art upon reviewing the above description. By way of example, the invention has been described primarily with reference to the use of a high density oligonucleotide array, but it will be readily recognized by those of skill in the art that other nucleic acid arrays, other methods of measuring transcript levels and gene expression monitoring at the protein level could be used. The scope of the invention should, therefore, be determined not with reference to the above description, but should instead be determined with reference to the appended claims, along with the full scope of equivalents to which such claims are entitled.

All references cited in this application are incorporated by reference for all purposes.

What is claimed is:

1. A method for determining an adjusted expression measurement for a target gene in a biological sample comprising:

measuring the expression of said target gene in said biological sample to obtain an expression measurement of said target gene and simultaneously measuring the expression of at least ten maintenance genes in said first biological sample to obtain an expression measurement for each of said at least ten maintenance genes wherein said at least ten maintenance genes are selected from the group consisting of the genes encoding Profilin, Thymosin beta-4 mRNA, Prothymosin alpha mRNA (ProT-alpha), Actin depolymerizing factor, Adducin gamma subunit, Myosin regulatory light chain, Non-muscle type cofilin, Myeloid cell differentiation protein (MCL1), G Protein Pathway Suppressor 1, Histone class C, Proteasome subunit HsC10-II, Nuclear ribonucleoprotein particle (hnRNP) C protein, ADP-ribosylation factor 1, Integral membrane protein calnexin, Esterase D, ATP-citrate lyase, AQP3 aquaporine 3 (water channel), and Voltage dependent anion channel isoform 1 (VDAC); and adjusting the expression measurement of said target gene using the expression measurement of each of said at least ten maintenance genes to obtain an adjusted expression measurement for said target gene in said biological sample.

2. The method of claim 1 wherein said adjusting comprises calculating an expression ratio of the expression measurement of said target gene over the expression measurement of said at least ten maintenance genes.

* * * * *

UNITED STATES PATENT AND TRADEMARK OFFICE
CERTIFICATE OF CORRECTION

PATENT NO. : 6,841,348 B1 Page 1 of 1
DATED : January 11, 2005
INVENTOR(S) : Warrington et al.

It is certified that error appears in the above-identified patent and that said Letters Patent is hereby corrected as shown below:

<u>Column 18,</u>
Line 26, delete "first".

Signed and Sealed this

Ninth Day of May, 2006

JON W. DUDAS
*Director of the United States Patent and Trademark Office*